United States Patent [19]

Green

[11] Patent Number: 4,773,420

[45] Date of Patent: Sep. 27, 1988

[54] PURSE STRING APPLICATOR

[75] Inventor: David T. Green, Norwalk, Conn.

[73] Assignee: U.S. Surgical Corporation, Norwalk, Conn.

[21] Appl. No.: 65,330

[22] Filed: Jun. 22, 1987

[51] Int. Cl.⁴ .............................................. B25C 5/06
[52] U.S. Cl. ................................ 128/334 R; 128/325; 227/19
[58] Field of Search .............. 128/334 R, 325, 334 C, 128/326, 327; 227/19, DIG. 1; 623/1

[56] References Cited

U.S. PATENT DOCUMENTS

| | | | |
|---|---|---|---|
| 3,472,231 | 10/1969 | Niebel et al. | 128/334 R |
| 3,519,187 | 7/1970 | Kapitanov et al. | 128/334 R |
| 3,540,431 | 11/1970 | Mobin-Uddin | 128/325 |
| 3,874,388 | 4/1975 | King et al. | 128/334 R |
| 3,908,662 | 9/1975 | Razgulov et al. | 128/334 R |
| 4,140,126 | 2/1979 | Choudhury | 623/1 |
| 4,577,631 | 3/1986 | Kreamer | 623/1 |
| 4,617,932 | 10/1986 | Kornberg | 128/334 R |

Primary Examiner—Richard C. Pinkham
Assistant Examiner—Gary Jackson
Attorney, Agent, or Firm—Kenyon & Kenyon

[57] ABSTRACT

The purse string applicator has a pair of tissue engaging arms which can be extended from the applicator to grasp apertured tissue and to subsequently flatten and move the engaged tissue over an anvil carrier. The arms are mounted on a tube which can be slid through a handle by means of a tissue knob held by a surgeon. The arms are also movable transversely by means of a control knob at the proximal end so as to engage and flatten the apertured tissue. A pair of handles are provided to staple a purse string about the apertured tissue after postioning of the tissue on the anvil carrier.

29 Claims, 4 Drawing Sheets

PURSE STRING APPLICATOR

This invention relates to a purse string applicator.

As is known, during an end-to-end anastomosis procedure, it is necessary to attach a so-called purse string to a section of tubular tissue in order to subsequently draw the apertured section of tissue together for a stapling operation. Various types of instruments have also been known for applying a purse string to the tissue. For example, U.S. patent application Ser. No. 928,988, filed Nov. 10, 1986 describes a purse string applicator which is capable of affixing a purse string about the aperture of a section of apertured tissue in a relatively simple and rapid manner. Generally, the purse string applicator requires the surgeon to insert an anvil carrier into a section of apertured tissue and to thereafter retract the anvil carrier into a position suitable for affixing one or more rows of staples and a purse string to and about the apertured tissue. In some cases, it may be difficult or inconvenient for a surgeon to insert the anvil carrier directly into an apertured tissue and to thereafter retract the anvil carrier while also pulling the apertured tissue with the anvil carrier into the retracted position for the stapling procedure.

Accordingly, it is an object of the invention to facilitate the positioning of a section of apertured tissue on a purse string applicator.

It is another object of the invention to provide a mechanized procedure for positioning a section of apertured tissue on a purse string applicator for the application of a purse string about the apertured tissue.

It is another object of the invention to provide a relatively simple construction for a purse string applicator for the positioning of apertured tissue onto an anvil carrier of the purse string applicator.

Briefly, the invention provides a purse string applicator which has a carrier such as an anvil carrier having anvils for receiving an apertured section of tissue, first means for positioning an apertured section of tissue over the anvils, which means is movable relative to the anvil carrier between an extended position to engage an apertured section of tissue and a retracted position within the anvil carrier, and second means for applying at least one row of staples with a purse string therein to a section of tissue received on the anvil carrier.

The means for positioning the apertured section of tissue over the anvils includes a pair of arms for engaging within an apertured section of tissue and which are mounted, for example on a common yoke which is connected to an elongated tube which is able to move the yoke and arms longitudinally relative to the axis of the anvil carrier between the extended and the retracted positions.

The purse string applicator is also constructed with a handle and an elongated tube extension which is secured to the handle at one end and which carries the anvil carrier at the opposite or distal end. The elongated tube which constitutes the mechanism or means for moving the tissue engaging arms longitudinally is also extended into the handle and is mounted therein so as to accommodate the movement of the arms. For example, a tissue knob is secured to a proximal end of the tube and is movable between a first position abutting the proximal end of the handle and a second position spaced from the handle which corresponds to the retracted position of the arms.

The tissue engaging arms are also mounted on the yoke so as to be movable transversely of the anvil carrier while an actuating means is provided for moving the arms transversely of the longitudinal axis of the anvil carrier. In this way, once the arms have been inserted into an apertured section of tissue, the arms can be spread apart to securely grip the tissue for movement of the tissues with the arms when the arms are retracted into the anvil carrier.

The actuating means includes an elongated rod which passes coaxially through the tube to which the yoke is connected and is mounted for relative movement relative to the tube and yoke while being connected to the arms so as to cause pivoting of the arms. To this end, the center rod cooperates with a rotatable control knob at the proximal end of the applicator so that by rotating the control knob, the tissue engaging arms can be pivoted.

The means for applying the staples to a section of tissue may include a pair of cartridge holders which are disposed on opposite sides of the anvil carrier for the mounting of staple cartridges thereon, a digitated pusher opposite each cartridge holder for expelling staples from a cartridge thereon and a pair of handles each of which is articulated to a pusher for moving the pusher towards and away from a respective cartridge holder. In this embodiment, the handles and the pushers are pivotally mounted on a common mounting block and are articulated to each other so that as the handles are brought together, the pushers also move towards each other into the respective staple cartridges for expelling staples towards the anvils of the anvil carrier.

The purse string applicator is such that a surgeon can readily manipulate the applicator to position a section of apertured tissue on the anvils of the anvil carrier in order to perform a subsequent purse string application procedure. For example, after the patient has been suitably prepared, the applicator can be positioned in close proximity to a section of apertured tissue. Thereafter, while the surgeon holds the handle of the applicator in one hand, the other hand of the surgeon can be used to slide the tissue knob forwardly into abutment with the handle so that the tissue engaging arms are placed within the apertured section of tissue. Thereafter, with the same hand, the surgeon can rotate the control knob so as to move the arms outwardly into engagement with the interior wall of the apertured tissue while flattening the tissue. Next, by grasping the tissue knob, the surgeon can pull the extended arms into the retracted position within the handle carrier while at the same time pulling the engaged and flattened tissue over the anvils of the anvil carrier.

After placement of the tissue on the anvil carrier, the arms may be brought together by rotating the control knob in the appropriate direction and the means for applying the staples with a purse string therein can be actuated to affix the purse string to the tissue. After securement of the purse string, the purse string applicator can be simply slid out of the tissue and discarded for subsequent cleaning or disposal.

These and other objects and advantages of the invention will become more apparent from the following detailed description taken in conjunction with the accompanying drawings wherein.

Figures 1, 2:
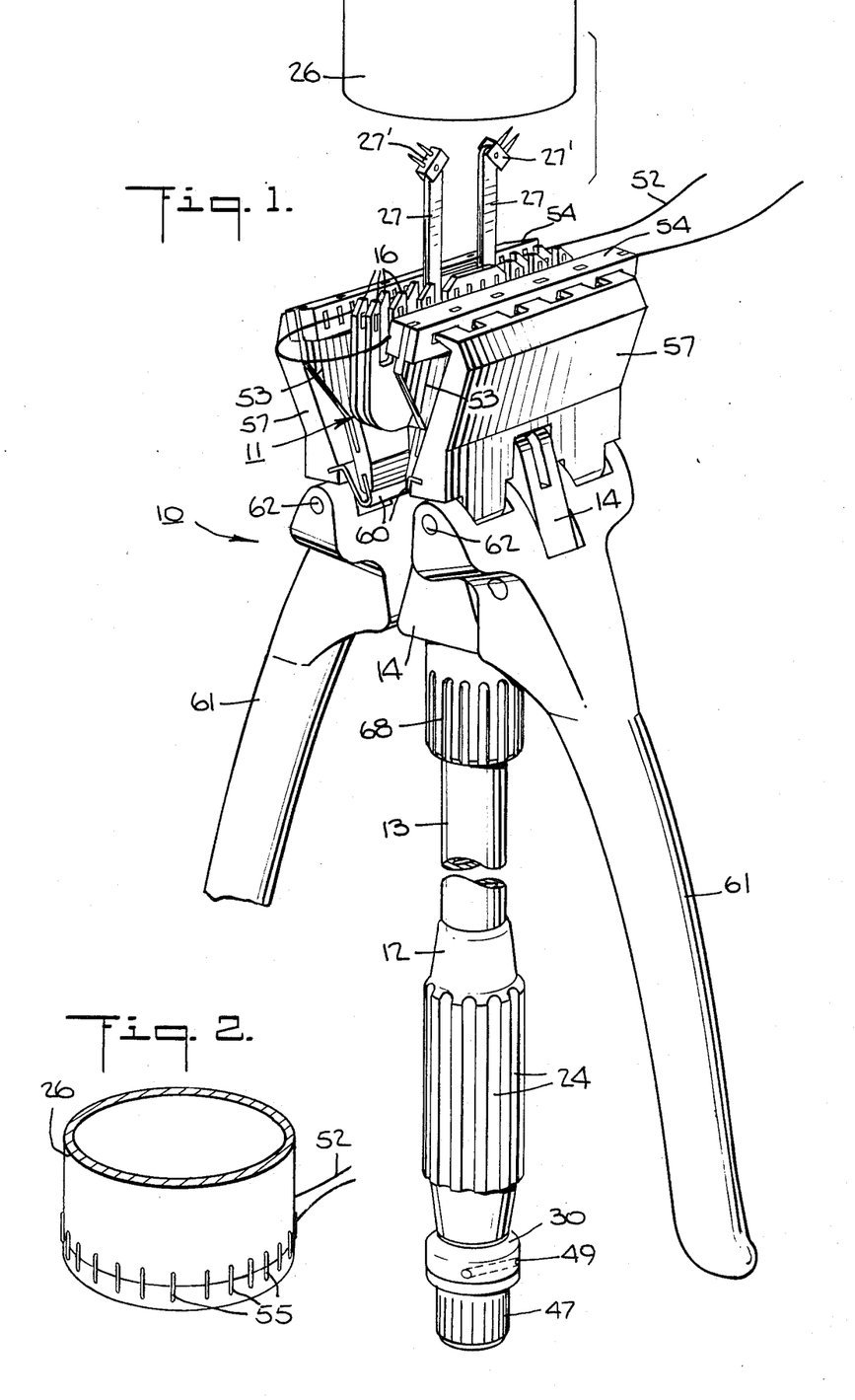
FIG. 1 illustrates a part perspective view of a purse string applicator constructed in accordance with the invention.
FIG. 2 illustrates a section of tissue having a purse string attached thereon in accordance with the invention.

Referring to FIG. 1, the purse string applicator 10 includes an anvil carrier 11, a handle 12 which is secured to the anvil carrier by means of an elongated tube extension 13 and a mounting block 14.

Figure 3:
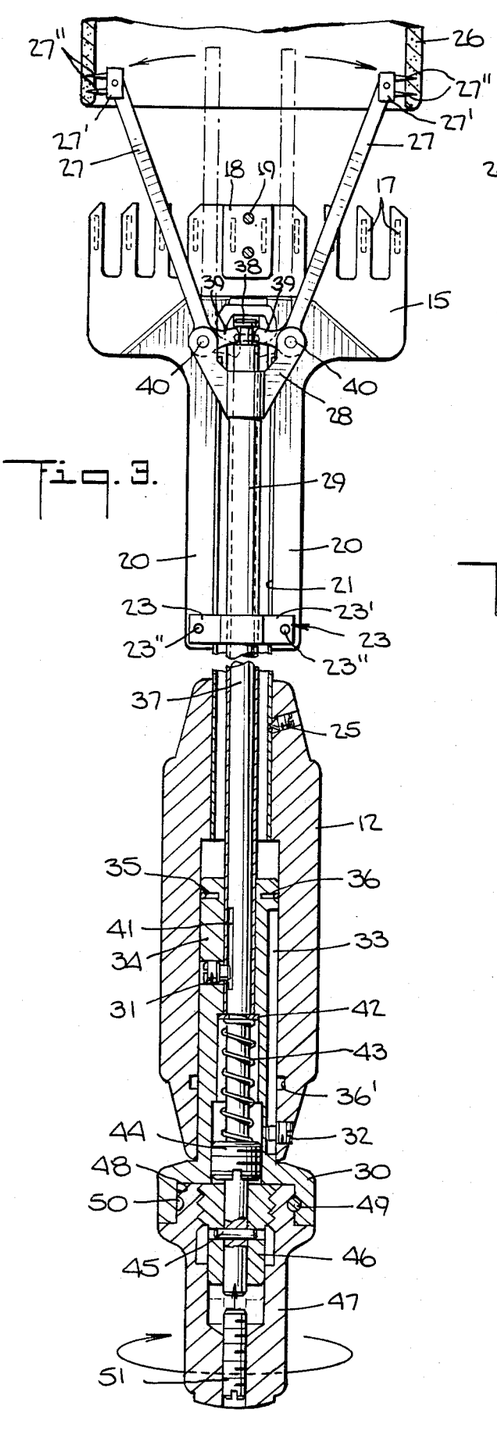
FIG. 3 illustrates a part cross sectional view of the actuating means for moving the tissue engaging arms longitudinally and transversely in accordance with the invention.

Referring to FIGS. 1 and 3, the anvil carrier 11 is formed of a pair of plates 15 which are disposed in spaced relation with each plate 15 having a plurality of spaced apart anvils 16 thereon. Each anvil 16 is provided with grooves or buckets 17 on an exterior side and the side walls of each may be provided with a serration in order to firmly grip an apertured section of tissue thereon. The plates 15 are spaced apart by a centrally located spacer 18 which is secured to each plate, for example by a pair of screws 19. As shown in FIG. 3, each plate 15 has an elongated stem 20 which is provided with an elongated slot 21.

Figure 4:
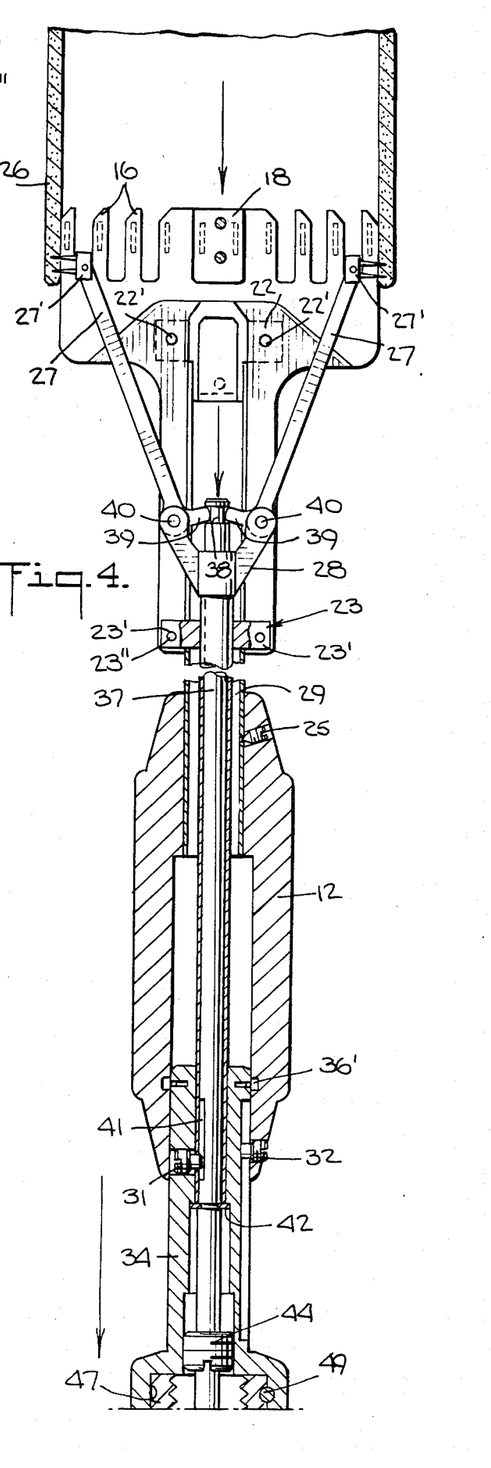
FIG. 4 illustrates a view similar to FIG. 3 with the tissue engaging arms in a retracted position in accordance with the invention.

As indicated in FIG. 4, the anvil carrier 11 is secured by a pair of noses 22 to the tube extension 13 at an upper end and by a spacer 23 to the tube extension 13 at the lower end. Each nose 22 bridges the slot 21 and is secured to a respective stem 20 by means of two screws 22'. Each nose 22 also has a central semi-circular section located over the distal end of the tube extension 13 and secured to the extension by a screw (not shown). The spacer 23 has a hollow central section slidably mounted inside the tube extension 13 and is secured thereto by two threaded screws (not shown). The spacer 23 also has a pair of flanges 23' extending from the central section through slots 69 in the tube extension 13 and between the stems 20 and which are secured to the stems 20 by screws 23''.

Referring to FIGS. 1 and 3, the handle 12 has a contoured surface, for example formed by longitudinal knurls or flutes 24 for gripping purposes. The tube extension 13 is slidably mounted in the distal end of the handle 12 and is secured thereto by means of a set screw 25 as indicated in FIG. 3.

Referring to FIGS. 1, 3 and 4, the applicator 10 is provided with a means for positioning an apertured section of tissue 26 over the anvils 16. For example, this means includes a pair of arms 27 which are movable relative to the anvil carrier 11 between an extended position an indicated in FIG. 3 to engage and flatten the apertured section of tissue 26 and a retracted position within the anvil carrier 11 as shown in FIG. 4. In addition, each arm 27 carries an outwardly directed tissue engaging means in the form of a small pivotally mounted plate 27' with two sharp teeth or prongs 27'' to penetrate into the tissue 26 to produce a firm grip.

The means for positioning the tissue 26 over the anvil 16 also includes a yoke 28 which is movably mounted within the anvil carrier 11 along a longitudinal axis and which has the arms 27 pivotally mounted thereon. In addition, an elongated tube 29 is secured to the yoke 28 for moving the yoke 28 and arms 27 relative to the anvil carrier 11.

Figure 5:
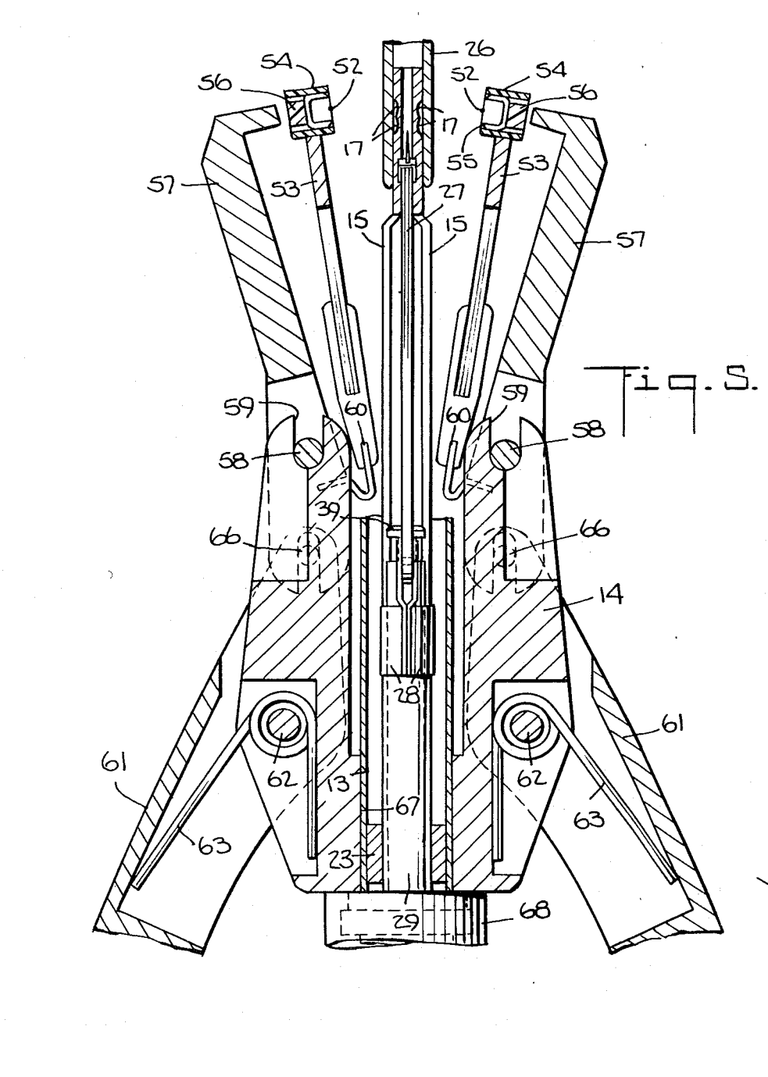
FIG. 5 illustrates a partial cross sectional view of the articulated means for applying staples with a purse string to a positioned section of tissue.

Referring to FIGS. 3 and 5, the yoke 28 is formed of two pieces which are secured together about the elongated tube 29 and which are fixed to the tube 29 by suitable means (not shown). The tube 29, in turn, is slidably mounted in the apertures of the spacers 23 and is disposed coaxially within the tube extension 13 to extend into the handle 12.

The means for positioning the tissue 26 over the anvil 16 also includes a tissue knob 30 (FIG. 3) of elongated shape which is secured to the tube 29 by a suitable means such as a set screw 31 and which is slidable within the handle 12 to move between a first position abutting the handle 12 as indicated in FIG. 3 and a second position spaced from the handle 12 and corresponding to the retracted position of the arms 27 as indicated in FIG. 4. The tissue knob 30 is restrained from rotating relative to the handle 12 by means of a set screw 32 which passes through the handle 12 into a longitudinally elongated slot 33 within an extension 34 of the knob 30. This extension 34 also has a circumferential groove 35 at a distal end which receives a split spring ring 36 which engages in a groove 36' in the wall of the handle 12 and serves as a detent when in the retracted position (FIG. 4).

Referring to FIG. 3, an actuating means is also provided for moving the arms 27 relative to the yoke 28 transversely of the longitudinal axis of the applicator 10. This means includes an elongated rod 37 which is movable along the longitudinal axis of the applicator 10 and which includes a means at the distal end in the from of a circumferential slot 38 which receives a lever 39 secured to each of the arms 27. The rod 37 moves relative to the tube 29, the arms 27 are caused to pivot on the yoke 28 via the levers 39, as indicated in FIG. 3, each arm 27 is pivotally mounted on the yoke 28 by means of a suitable pivot pin 40 or the like.

The center rod 37 also passes through the extension tube 13 into and through the handle 12. In this respect, the rod 37 is provided with a slot 41 at an intermediate point to receive a threaded end of the set screw 31 which secures the tissue knob 30 to the tube 29. This slot 41 is of a length to determine the excursion of the rod 37 relative to the tube 29. The rod 37 is also provided with an annular groove within which a washer 42 is seated to form an abutment for a spring 43 disposed about the rod 37. A retaining screw 44 is also threaded into the tissue knob 30 to abut the opposite end of the spring 43. The spring 43 thus serves to bias the rod 37 towards the distal end.

At the proximal end, the rod 37 is secured via a pin 45 to a lead screw 46 which, in turn, is threaded into a control knob 47.

The control knob 47 is rotatably mounted within a recess 48 of the tissue knob 30 and is held in place by means of a pin 49 which is received within a circumferential groove 50 of the control knob 47 and a suitable bore in the tissue knob 30. The control knob 47 is also provided with a central aperture in which a threaded stop screw 51 is mounted.

Upon rotation of the control knob 47, the locking screw 46 is caused to move proximally or distally as the case may be and thus cause a similar movement of the center rod 37. This, in turn, causes the arms 27 to pivot toward or away from each other as the case may be.

Referring to FIGS. 1 and 5, the applicator 10 is also provided with a means for applying at least one row of staples with a purse string 52 therein to the tissue 26 which is received on the anvil carrier 11. This means includes a pair of cartridge holders 53 which are disposed on opposite sides of the anvil carrier 11 for mounting of staple cartridges 54 thereon. As indicated in FIG. 5, each staple cart ridge 54 includes one row of staples 55 (only one of which is shown) and a common pusher element 56 for ejecting the row of staples 55 simultaneously. A purse string 52 is also mounted across the face of the cartridge 54 between the legs of each staple. As also indicated, the staples 55 are disposed opposite the buckets 17 of each anvil plate 15.

In addition, the staple applying means includes a digitated pusher 57 opposite each cartridge holder 53 for expelling the staples 55 from the cartridge 54 thereon. As indicated, each pusher 57 is pivotally mounted via a pivot pin 58 on the mounting block 14. To this end, the mounting block 14 has a pair of saddle-shaped recesses 59 at the upper ends, as viewed, to receive the pivot pins 58.

Each cartridge holder 53 is mounted on a pusher 57 by means of a leaf spring 60 for purposes as described below.

The staple applying means also includes a pair of handles 61 which are pivotally mounted to the mounting block 14 via suitable pivot pins 62. Each handle 61 is also biased by a spring 63 into an outward position as illustrated in FIG. 1. Each spring 63 is further disposed about a respective pivot pin as indicated in FIG. 5 and is suitably received within recesses 64,65 in the mounting block 14 and handle 61, respectively. Each handle 61 is also articulated by means of a pivot pin 66 to a pusher 57 so that when the handles are pivoted inwardly towards each other, the pushers 57 are also pivoted towards each other.

As indicated in FIG. 5, the mounting block 14 is provided with a central aperture 67 through which the tube extension 13 passes. If desired, a suitable locking collar 68 is fitted to the tube extension 13 against the mounting block 14 (see FIG. 5) to hold the tube extension 13 in position when firing the staples.

Referring to FIGS. 3 and 5, the tube extension 13 is provided with a pair of diametrically opposed slots 69 each of which is sized so as to accomodate passage of the yoke 28 therethrough as well as passage of the arms 27. Further, each slot is of a length to accomodate the longitudinal excursion of the yoke 28.

In use, the applicator 10 is first positioned near the section of aperture tissue 26 which is to be provided with the purse string 52. Next, while holding the handle 12 in one hand, the tissue knob 30 is grasped by a second hand and moved distally into the handle 12 into a position as indicated in FIG. 3. At this time the arms 27 are initially in a parallel relationship as indicated in FIG. 1. Next, the control knob 47 is rotated so as to cause the arms 27 to pivot outwardly of each other into engagement with the interior wall of the tissue 26 to flatten the tissue 26 as indicated in FIG. 3. At the same time, the sharp prongs 27″ of the tissue engaging means penetrate into the tissue 26 to firmly grip the tissue 26. In this respect the plates 27′ on which the teeth 27″ are mounted may pivot to a limited degree to accommodate the penetrating action of the teeth 27″ without tearing the tissue 26.

After engagement, the tissue knob 30 is withdrawn from the handle 12 in the direction indicated in FIG. 4 so as to move the engaged tissue 26 over the anvil plates 15. In this respect, the arms 27 slide into the space between the anvil plates 15 while at the same time guiding the tissue 26 over and about the anvils 16. In this respect, the anvil 16 are shaped so as to facilitate sliding of the tissue 26 along the sides of the plates 15 as well as over the outer edges of the plates 15.

As indicated in FIG. 4, the arms 27 are retracted into a position below the level of the buckets 17 in the anvils 16.

Figure 6:
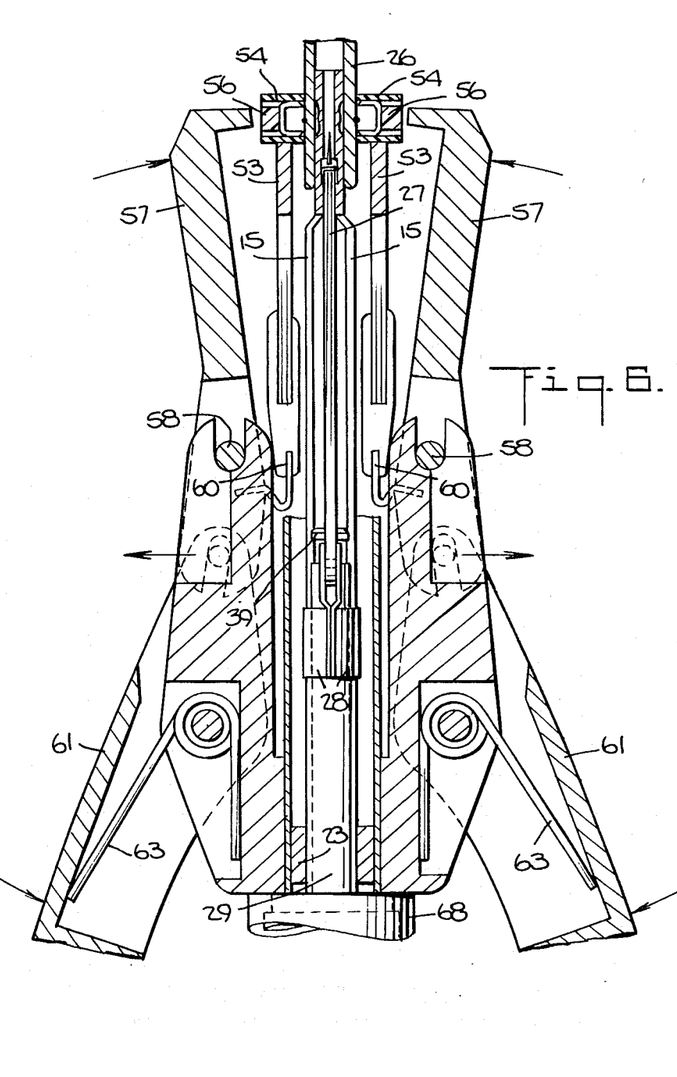
FIG. 6 illustrates a view of the applicator at a point during application of a row of staples to opposite sides of the aperture tissue.
Figure 8:
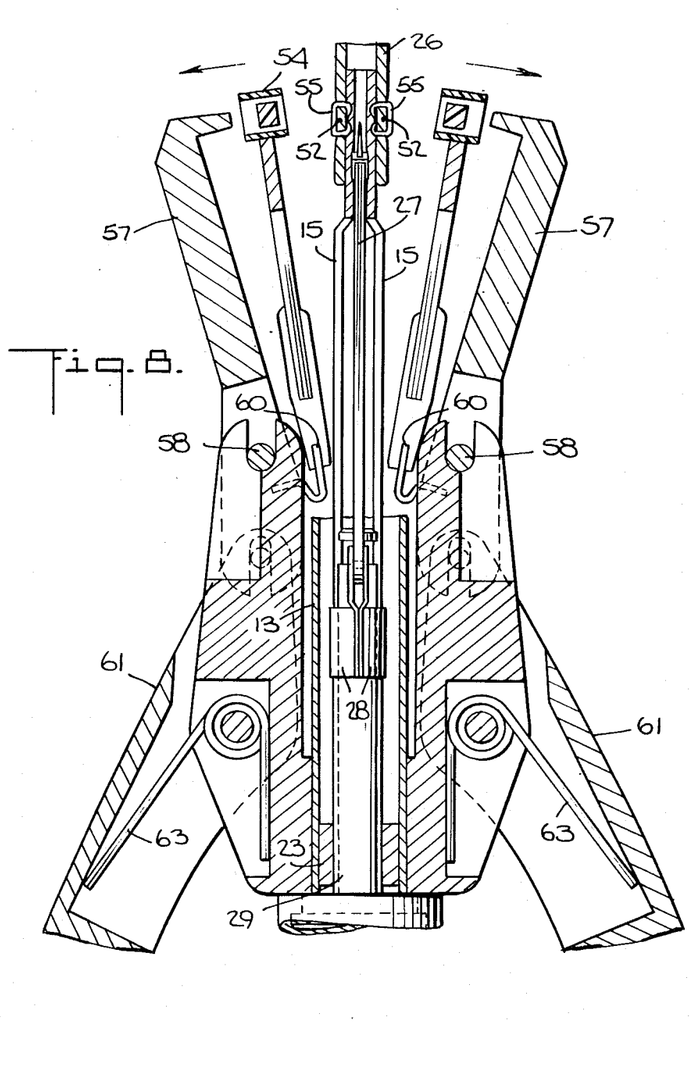
FIG. 8 illustrates a view similar to FIGS. 5, 6 and 7 after a clinching step.

After positioning of the tissue 26 on the anvil carrier 11, the two handles 61 are gripped while the central handle 12 remains held in the original hand. The pivotal handles 61 are then brought together as indicated in FIG. 6 so as to move the digitated ends of the pushers 57 into the respective cartridges 54 to expel the staples 55 through the tissue 26 and against the anvils 16. The force applied should be sufficient to cause the staples 55 to become clinched via the bucket 17. After clinching, the handles 61 are released so that the handles 61 are biased outwardly by the torsion springs 63 into the position indicated in FIG. 8.

Figure 7:
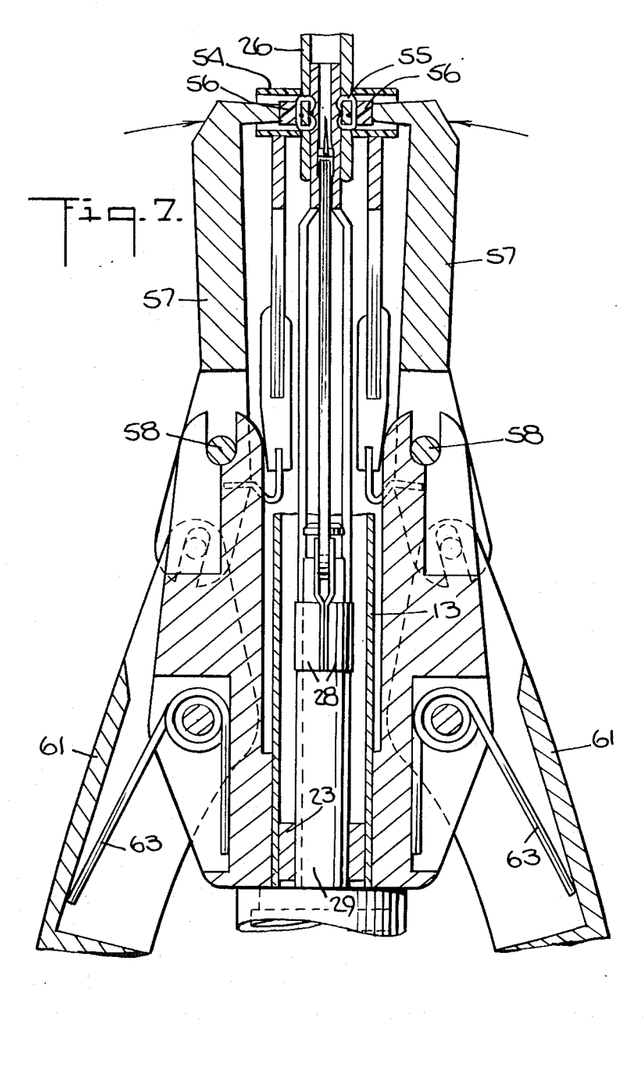
FIG. 7 illustrates a view similar to FIG. 6 at a point during clinching of the staples.

Of note, when the pushers 57 are being brought towards each other, the cartridge holders 53 are first moved against the tissue 26 so as to position the staples 55 and the purse string 52 against the outside surface of the tissue 26 as indicated in FIG. 6. Continued movement of the pushers 57 causes the common element 56 in each cartridge 54 to push the staples 55 through the tissue 26 while bringing the purse string 52 against the outside surface of the tissue 26 as indicated in FIG. 7. After the handles 61 are released, the pushers 57 spring back into the position indicated in FIG. 8. At the same time, the cartridge holders 53 spring back into the relaxed position. The applicator 10 can then be removed by sliding the anvil carrier 11 from within the tissue 26. The tissue 26 then has a purse string 52 secured thereon by the staples 55 as indicated in FIG. 2.

The invention thus provides a purse string applicator which can be readily manipulated to position an apertured section of tissue in place for the application of a purse string thereon without need for a surgeon to touch the tissue section for positioning over an anvil carrier.

Further, the invention provides an applicator which can be readily manipulated by a surgeon using two hands, one to hold the applicator and a second to flatten and move apertured tissue into place on the applicator and to thereafter staple a purse string onto the apertured tissue.

The invention permits an applicator to be positioned in place within a patient and to thereafter permit the tissue to be provided with a purse string to be brought to the applicator in a relatively simple manner.

The purse string applicator may also be modified so as to accommodate staples which need not pass entirely through the tissue. In this respect, the carrier for receiving the apertured section of tissue need not have pockets. Further, the carrier may be made without anvils. In this latter respect, the carrier would be constructed to receive the flattened and spread out tissue in a manner as described above prior to application of the purse string via a row of staples which bite into the tissue without penetrating there through. Of course, the anvils may remain simply to provide a backing against which the staple-applying forces may react.

What is claimed is:

1. A purse string applicator comprising
   a carrier for receiving an apertured section of tissue;
   first means for positioning an apertured section of tissue over said carrier, said means being movable relative to said carrier between an extended position to engage an apertured section of tissue and a retracted position within said carrier; and
   second means for applying at least one row of staples with a purse string therein to a section of tissue received on said carrier.

2. A purse string applicator as set forth in claim 1 wherein said first means includes a yoke movably mounted within said anvil carrier along a longitudinal axis, a pair of arms mounted on said yoke for engaging an apertured section of tissue and an elongated tube secured to said yoke for moving said yoke relative to said anvil carrier.

3. A purse string applicator as set forth in claim 2 wherein said first means further includes actuating means for moving said arms relative to said yoke transversely of said longitudinal axis.

4. A purse string applicator as set forth in claim 3 wherein each arm includes a lever at a proximal end and said actuating means includes an elongated rod movable along said longitudinal axis and having a circumferential slot receiving said lever of each arm for moving said arms transversely in response to longitudinal movement of said rod.

5. A purse string applicator as set forth in claim 4 wherein said actuating means includes a lead screw secured to a proximal end of said rod and a control knob threadably engaging said lead screw and rotatably mounted relative to said tube for moving said lead screw and said rod along said longitudinal axis in response to rotation of said control knob about said axis.

6. A purse string applicator as set forth in claim 4 wherein said rod extends coaxially within said tube.

7. A purse string applicator as set forth in claim 4 which further comprises a handle, a tube extension secured to and extending from said handle, and means securing said carrier to a distal end of said tube extension.

8. A purse string applicator as set forth in claim 7 wherein said tube is movably mounted in said handle and said tube extension for movement along said longitudinal axis.

9. A purse string applicator as set forth in claim 8 which further comprises a tissue knob secured to said tube for movement therewith and having said control knob rotatably mounted therein.

10. A purse string applicator as set forth in claim 9 wherein said tissue knob is movable between a first position abutting said handle and corresponding to said extended position of said arms and a second position spaced from said handle and corresponding to said retracted position of said arms.

11. A purse string applicator as set forth in claim 1 wherein said carrier includes a pair of plates disposed in spaced relation and on opposite sides of said first means, each said plate having a plurality of spaced apart anvils thereon.

12. A purse string applicator as set forth in claim 1 wherein said second means includes a pair of cartridge holders disposed on opposite sides of said carrier for mounting of staple cartridges therein, a digitated pusher opposite each cartridge holder for expelling staples from a staple cartridge thereon, and a pair of handles, each said handle being articulated to a pusher for moving said pusher towards and away from a respective cartridge holder.

13. A purse string applicator as set forth in claim 12 which further comprises a mounting block having said handles pivotally mounted thereon.

14. A purse string applicator as set forth in claim 13 wherein said first means includes a yoke movably mounted within said carrier along a longitudinal axis, a pair of arms mounted on said yoke for engaging an apertured section of tissue and an elongated tube secured to said yoke and movably mounted in said mounting block for moving said yoke relative to said carrier.

15. A purse string applicator comprising
   an anvil carrier having anvils for receiving an apertured section of tissue;
   a handle secured to said anvil carrier;
   a pair of arms for engaging an apertured section of tissue;
   a yoke secured to said arms; and
   an elongated tube secured to said yoke and movably mounted within said handle for moving said yoke relative to said anvil carrier along a longitudinal axis between an extended position to engage said arms with an apertured section of tissue and a retracted position to position said arms within said anvil carrier with the apertured section of tissue over said anvil carrier.

16. A purse string applicator as set forth in claim 15 wherein each said arm is pivotally mounted on said yoke.

17. A purse string applicator as set forth in claim 16 which further includes actuating means for moving said arms relative to said yoke transversely of said longitudinal axis.

18. A purse string applicator as set forth in claim 17 wherein each arm includes a lever at a proximal end and said actuating means includes an elongated rod movable along said longitudinal axis and having a circumferential slot receiving said lever of each arm for moving said arms transversely in response to longitudinal movement of said rod.

19. A purse string applicator as set forth in claim 15 wherein said anvil carrier includes a pair of plates disposed in spaced relation with said arms therebetween, each said plate having a plurality of said anvils thereon.

20. A purse string applicator comprising
   a handle;
   an anvil carrier having anvils for receiving an apertured section of tissue;
   an elongated tube extension secured to and between said handle and said anvil carrier;
   first means for engaging an apertured section of tissue; and
   second means extending through said handle and said tube extension means relative to said anvil carrier between an extended position to engage an apertured section of tissue and a retracted position to position the apertured section of tissue over said anvil carrier.

21. A purse string applicator as set forth in claim 20 wherein said second means includes a tube extending coaxially through said tube extension and a tissue knob secured to said tube and abutting said handle with said first means in said extended position.

22. A purse string applicator as set forth in claim 21 which further comprises a pair of spacer means secured to said anvil carrier and slidably guiding said tube therein on a longitudinal axis.

23. A purse string applicator as set forth in claim 22 wherein said first means includes a yoke disposed between said pair of spacer means and a pair of arms mounted on said yoke for engaging apertured section of tissue.

24. A purse string applicator as set forth in claim 23 which further includes actuating means for moving said arms relative to said yoke transversely of said longitudinal axis.

25. A purse string applicator as set forth in claim 24 wherein each arm includes a lever at a proximal end and said actuating means includes a rod movable within said tube and engaging said lever of each arm for pivoting said arms transversely of said anvil carrier in response to longitudinal movement of said rod.

26. A purse string applicator as set forth in claim 25 wherein said actuating means includes a lead screw secured to a proximal end of said rod and a control knob threadably engaging said lead screw and rotatably mounted relative to said tube for moving said lead screw and said rod along said longitudinal axis in response to rotation of said control knob about said axis.

27. A purse string applicator as set forth in claim 20 wherein said first means includes a pair of movably mounted arms and which further comprises means for moving said arms transversely of a longitudinal axis of said anvil carrier.

28. A purse string applicator as set forth in claim 27 wherein said means for moving said arms includes a rotatable control knob on said second means adjacent a proximal end of said handle for moving said arms transversely in response to rotation of said control knob.

29. A purse string applicator as set forth in claim 28 wherein said second means includes a tube extending coaxially through said tube extension and a tissue knob secured to said tube and abutting said handle with said first means in said extended position.

* * * * *

UNITED STATES PATENT AND TRADEMARK OFFICE
CERTIFICATE OF CORRECTION

PATENT NO. : 4,773,420

DATED : September 27, 1988

INVENTOR(S) : David T. Green

It is certified that error appears in the above-identified patent and that said Letters Patent is hereby corrected as shown below:

Title page:

```
In the Abstract, line 11 "postioning" should be -positioning-
Column 3, line 64 "an" should be -as-
Column 5, line 13 "cart ridge" should be -cartridge-
Column 5, line 51 "accomodate" should be -accommodate-
Column 5, line 53 "accomodate" should be -accommodate-
Column 6, line 10 "anvil 16" should be -anvils 16-
Column 7, line 1 "there through" should be -therethrough-
```

Signed and Sealed this

Twenty-first Day of March, 1989

Attest:

DONALD J. QUIGG

*Attesting Officer*  *Commissioner of Patents and Trademarks*